United States Patent [19]

Chick et al.

[11] Patent Number: 5,002,661

[45] Date of Patent: Mar. 26, 1991

[54] ARTIFICIAL PANCREATIC PERFUSION DEVICE

[75] Inventors: William L. Chick, Wellesley; Susan J. Sullivan, Newton; Kermit M. Borland; John M. Harvey, both of Worcester; Thomas E. Muller, Concord; Karen E. Dunleavy, Billerica; Donald P. King, Jr., Haverhill; Edward J. Doherty, Waltham; Barry A. Solomon, Bedford; Amy L. Foley, Framingham, all of Mass.

[73] Assignee: W.R. Grace & Co.-Conn., Lexington, Mass.

[21] Appl. No.: 398,739

[22] Filed: Aug. 25, 1989

[51] Int. Cl.$^5$ .............................................. B01D 63/06
[52] U.S. Cl. .................................... 210/192; 210/209; 210/321.78; 210/321.87; 424/424; 435/284; 604/4; 604/175
[58] Field of Search .............. 210/192, 321.78, 321.87, 210/321.79, 321.88, 321.8, 321.89, 209, 198.1; 604/4, 175; 435/283, 284, 285, 286; 424/424, 101

[56] References Cited

U.S. PATENT DOCUMENTS

| | | | |
|---|---|---|---|
| 3,827,565 | 8/1974 | Matsumura | 210/321.75 |
| 4,169,477 | 10/1979 | Bokros | 604/175 |
| 4,242,459 | 12/1980 | Chick | 210/321.74 |
| 4,242,460 | 12/1980 | Chick et al. | 210/321.78 |
| 4,323,457 | 4/1982 | Lun et al. | 210/321.87 |
| 4,378,016 | 3/1983 | Loeb | 424/424 |
| 4,578,191 | 3/1986 | Jaffrin et al. | 210/321.87 |

FOREIGN PATENT DOCUMENTS

EPO 0127989 12/1984 European Pat. Off. .
WO 85/05630 12/1985 PCT Int'l Appl. .

OTHER PUBLICATIONS

Chick, W. L. et al., *Science*, 187: 847-849 (1975).
Chick, W. L. et al., *Trans. Amer. Soc. Artif. Int. Organs*, XXI: 8-14 (1975).
Sun, A. M., et al., *Diabetes*, 26(12): 1136-1139 (1977).
Chick, W. L. et al., *Science*, 197: 780-782 (Aug. 19, 1977).
Whittemore, A. D., et al., *Trans. Am. Soc. Artif. Intern. Organs*, XXIII: 336-340 (1977).
Galletti, P. M. et al., *European Soc. Art. Organs*, 5: 132-135 (1978).
Naber, S. P. et al., *Intl. Cong. Series No. 500 Diabetes*, 1979, pp. 227-231.
Tze, W. J. et al., *Diabetologia*, pp. 247-252 (1979).
Weinless, N. J. and Colton, C. K., *Ann. N.Y. Acad. Sci.*, 413: 421-423 (1983).
Reach, G. et al., *Diabetes*, 33: 752-761 (1984).
Colton, C. K. et al., "Development ... Pancreas", pp. 541-555.
Araki, Y. et al., *Diabetes*, 34: 850-854 (Sep. 1985).

*Primary Examiner*—W. Gary Jones
*Attorney, Agent, or Firm*—Hamilton, Brook, Smith & Reynolds

[57] ABSTRACT

A device which serves as an artificial pancreas comprises a hollow fiber having an inner diameter of about .5 mm which is surrounded by islets of Langerhans enclosed in a housing. The islets are suspended in a semi-solid matrix which ensures desired distribution of the cells about the hollow fiber. The hollow fiber and suspended islets are enclosed in a housing which further aids the desired distribution of islets about the hollow fiber. The hollow fiber has a porosity which selectively allows passage of substances having a molecular weight of less than about 100,000 Daltons. The semi-solid matrix in which the islets are embedded and suspended is formed of an appropriate supporting material such as alginate or agar.

33 Claims, 8 Drawing Sheets

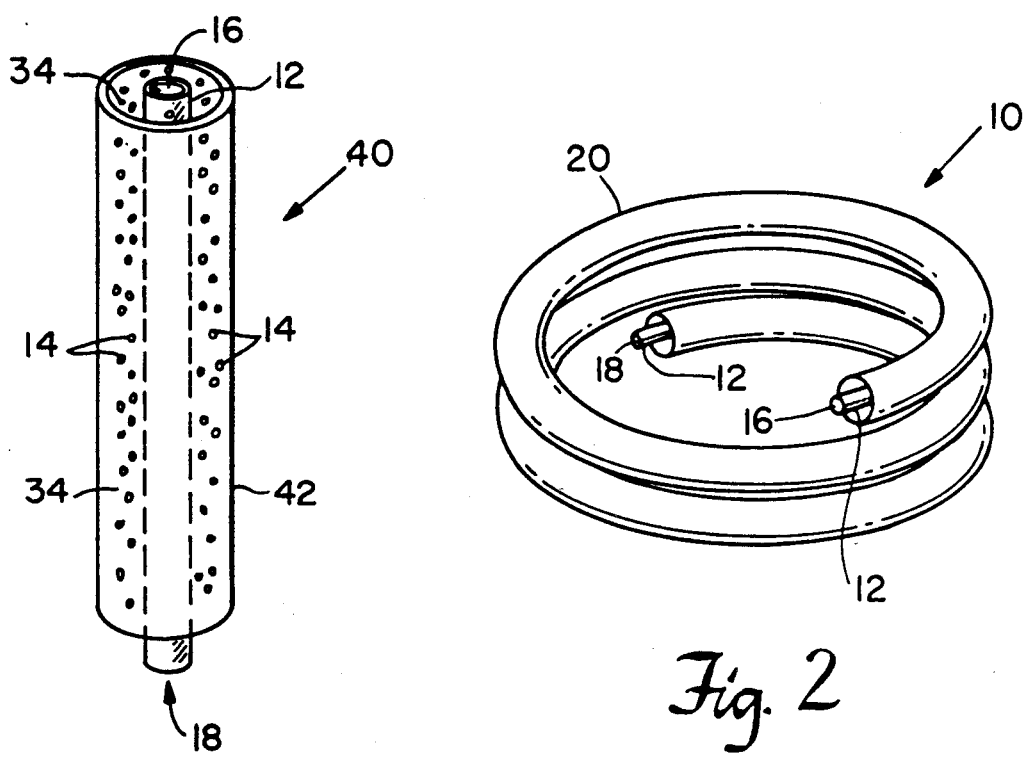
Fig. 1
Fig. 2
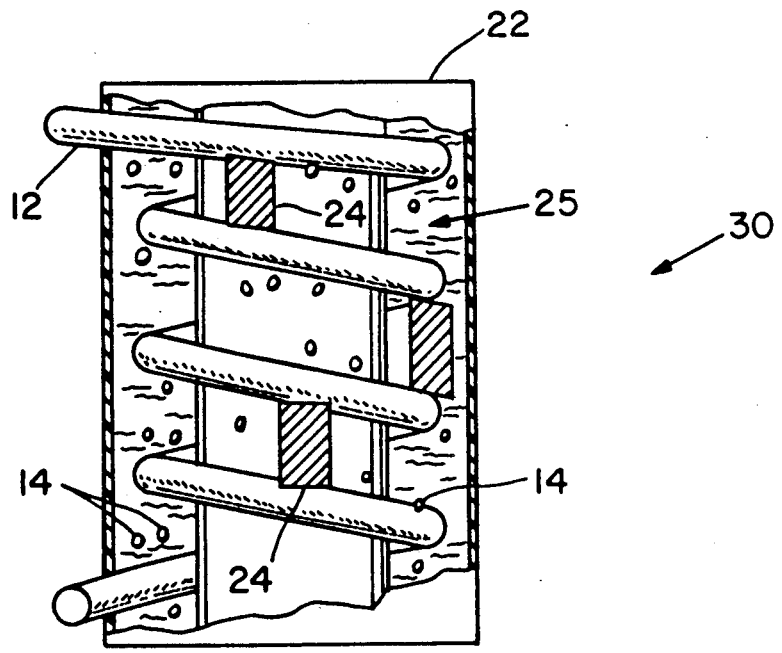
Fig. 3a

ARTIFICIAL PANCREATIC PERFUSION DEVICE

BACKGROUND OF THE INVENTION

Beta cells, the insulin-producing cells of the pancreas, comprise more than 70% of the cell population found in discrete collections of cells in the pancreas which are known as islets of Langerhans. Some major effects of insulin are to increase the uptake of glucose by various tissues including muscle and fat and to decrease glucose output by the liver. Either absolute or relative insulin deficiency impairs glucose uptake and increases hepatic glucose output thereby resulting in the abnormally high blood glucose concentrations characteristic of diabetes mellitus.

Insulin release from pancreatic islets is controlled by a combination of factors, including the concentration of glucose and other nutrients in the blood, gastrointestinal hormones and neuronal stimuli. In humans, glucose is the principal stimulus for insulin secretion from beta cells. However, other fuels such as amino acids and fatty acids also promote secretion.

Diabetes is generally characterized by an elevated concentration of glucose in the blood and urine. Insulin is administered to a diabetic patient in an effort to control or regulate the concentration of glucose and other nutrients in the blood. The objective of this regimen is to maintain glucose levels close to normal. One possible reason for the failure of this treatment to prevent the complications associated with diabetes is that daily insulin injections do not mimic the rapid insulin secretory responses of normal islets to physiological demand. Consequently, there has been a great deal of interest in developing a treatment for diabetics which would make it possible to maintain normal blood glucose levels at all times, an objective extremely difficult or impossible to achieve by insulin injections, diet and exercise.

Attempts have been made to produce an electromechanical artificial pancreas system comprised of, a glucose sensor, an information processor and an insulin pump to mimic physiological response patterns for insulin release. Thus far, this approach has not been effective.

Another approach to treating diabetes is replacement of the malfunctioning organ by transplantation of normal pancreatic tissue. However, transplantation of pancreatic tissue has met with limited success due to problems of tissue typing, donor availability and immune rejection.

To address these problems, researchers have focused on creating a hybrid artificial pancreas which mimics the organ's physiological response to glucose levels. Artificial pancreatic devices containing live islets have been designed to avoid immune rejection. These devices contain a semipermeable membrane which separates the transplanted islets from immunoreactive cells and molecules.

Matsumura describes an artificial pancreas device which includes a semipermeable membrane on one side of which once-dispersed live pancreatic islets are placed. (U.S. Pat. No. 3,827,565).

Sun et al. (U.S. Pat. No 4,323,457 (1982)) describe another artificial pancreatic device which is a container means through which a hollow fiber of 500 $\mu$m diameter is passed. The container holds pancreatic islets and the fiber is described as having a porosity which allows for passage of substances of molecular weight less than 100,000 Daltons.

Chick et al. (U.S. Pat. No. 4,242,459 and U.S. Pat. No. 4,242,460 (1980)) describe a cell culture device having a generally circular fluid-tight cavity and a semipermeable tube wrapped about itself to form coils. Another cell culture device comprises a housing and a stationary spool about which a semipermeable tube is wrapped to form coils.

None of the presently-available artificial pancreatic devices solve the problems associated with diabetes and with implantation of an artificial device into an individual. Thus, there is a need for a pancreatic device containing viable islets of Langerhans which can be implanted into a diabetic individual and be effective in controlling blood glucose levels in such a way as to mimic normal physiological response to changing blood glucose concentrations.

SUMMARY OF THE INVENTION

The present invention provides an artificial organ perfusion device, in particular an artificial pancreatic perfusion device which results in the secretion of insulin into the blood of an individual in response to changes in blood glucose concentrations. The device employs a hollow fiber for passage of blood through a housing which contains pancreatic islets of Langerhans in an appropriate supporting material and a connecting means for connecting a blood vessel, such as a vein or an artery, to the ends of the hollow fiber to provide continuous flow from the individual, through the device and back into the individual. The islets are introduced into the housing suspended in a supporting material, such as a semi-solid matrix which contains agar, alginate or other suitable medium, such that the islets are distributed about the length of the hollow fiber. The hollow fiber has a porosity which allows only substances of molecular weight less than about 100,000 Daltons to pass transversely therethrough while carrying blood along the length of the fiber. Substances of molecular weight below this cutoff, including substances which stimulate insulin secretion, such as glucose, amino acids, fatty acids, hormones (e.g., thyroxine, growth hormone, glucocorticoids), and neuronal stimuli diffuse through the hollow fiber wall to the islets. In response to these substances, the islets produce insulin, which diffuses transversely through the hollow fiber wall into the blood flowing within the fiber. The insulin-containing blood flows from the device and into the individual's circulation through an outlet end of the fiber.

Preferably, the hollow fiber has an inner diameter which is complementary to the inner diameter of a blood vessel connected by connecting means to the ends of the fiber. As a result, a smooth and continuous flow of blood occurs from the body through the hollow fiber and back into the body. Islets remain viable and produce insulin because necessary substances (e.g., nutrients and oxygen) are provided by the blood flowing therethrough. The blood flowing therethrough also carries away waste products produced by the cells within the device.

The hollow fiber has a pore size which selectively allows passage of substances of less than about 100,000 Dalton MW, to provide a barrier to protect the xenograft from a host immune reaction. Hence, the pancreatic islets need not match the tissue type of the individual to be treated through use of the subject invention.

The inner walls of the housing are spaced apart from the hollow fiber in a manner which defines a chamber about the hollow fiber along the length of the fiber. Preferably, the inner walls of the housing are positioned sufficiently close to the hollow fiber to maximize the diffusion of substances to and from the fiber. It is within this chamber that the semi-solid matrix in which islets are suspended (referred to as an islet suspension) is introduced to substantially fill the chamber. Preferably, the islet suspension not only substantially fills the chamber, but distributes the pancreatic islets circumferentially and longitudinally along the length of the fiber. A minimized distance between the islets and the fiber maximizes diffusion of substances, such as glucose, from the blood flowing within the hollow fiber transversely through the fiber wall to the islets and also maximizes the passage of insulin through the fiber wall into the blood flowing within the fiber.

In one embodiment of the present invention, the hollow fiber lies substantially straight and uncurved coaxially within a tubular housing. Between the inner walls of the tubular housing and the outer walls of the hollow fiber, pancreatic islets are preferably distributed circumferentially and longitudinally about the fiber, for example, by means of a semi-solid matrix.

In another embodiment the housing is coaxially positioned about the hollow fiber along the length of the fiber. The housing together with the hollow fiber are coiled about a longitudinal axis. The pancreatic islets are distributed about the fiber in the coiled housing.

In a preferred embodiment, the hollow fiber alone is coiled into one or more loops about a longitudinal axis, and enclosed in an annular shaped housing. In this configuration, each loop of the coiled hollow fiber may be spaced apart from preceding and succeeding loops by spacers. The spacers insure a gap between each loop of the hollow fiber, and in turn make it possible to distribute the islets circumferentially and longitudinally along the length of the fiber. The annular shaped housing is light weight and has a finished outer shape which facilitates implantation into an individual.

Thus, the device of the present invention contains viable islets of Langerhans and can be implanted into a diabetic individual. The islets secrete insulin in response to blood glucose levels. The insulin diffuses across the fiber wall and into the individual's bloodstream. The hollow fiber is tissue compatible and has a porosity which selectively allows passage of substances such as glucose and insulin across the fiber wall.

BRIEF DESCRIPTION OF THE DRAWINGS

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a schematic view of an artificial pancreatic perfusion device generally embodying the present invention.

FIG. 2 is a schematic view of another artificial pancreatic perfusion device embodying the present invention and having a coiled housing.

FIG. 3a is a schematic view partially cut away of another embodiment of the present invention having an annular housing.

FIG. 3b is a plan view of the embodiment of FIG. 3a.

DETAILED DESCRIPTION OF THE PREFERRED EMBODIMENT

Figure 3B:
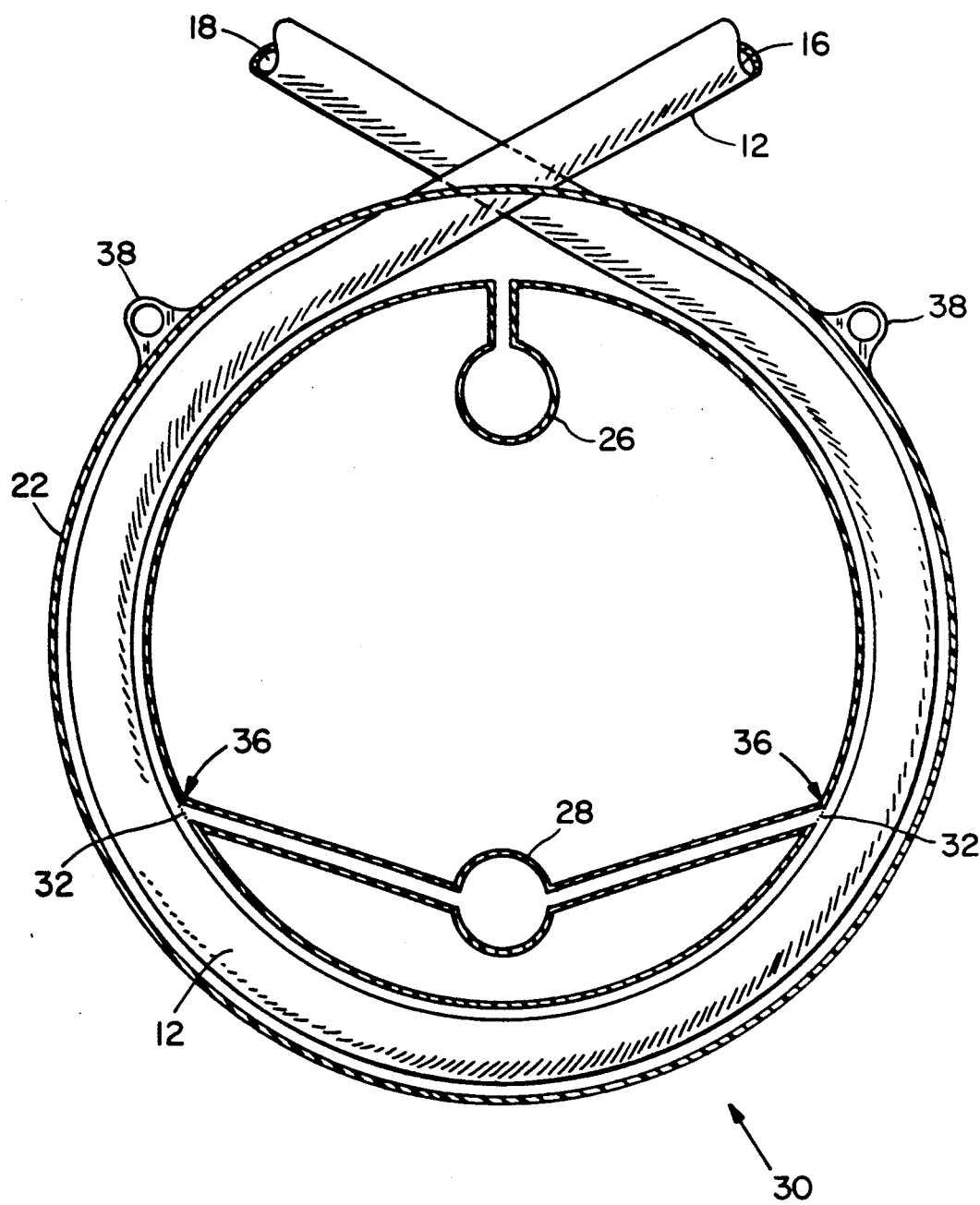

The present invention relates to a device useful for controlling fluctuations in blood glucose levels, as well as to a method of treating such fluctuations, particularly in individuals with diabetes. The device includes viable intact pancreatic islets of Langerhans, islet fragments, beta cells, or a combination thereof, which sense and respond to blood glucose levels as blood flows through a hollow fiber which selectively allows passage of molecules having a molecular weight of less than about 100,000 Daltons. The term hollow fiber is meant to encompass various hollow, tissue compatible materials capable of transporting a medium (i.e., blood) and having a selected porosity which selectively allows the passage of substances across the material.

An artificial pancreatic perfusion device embodying the present invention is illustrated in FIG. 1 and generally referenced as 40. The device provides a hollow fiber 12 surrounded by islets of Langerhans 14.

Blood from an individual enters hollow fiber 12 through inlet end 16 and flows within hollow fiber 12, along the length of fiber 12 toward outlet end 18. Hollow fiber 12 is a porous membrane with pore size which selectively allows transverse passage of substances having a molecular weight of less than about 100,000 Daltons. Thus, the pores allow diffusion of glucose and necessary nutrients from the blood through the walls of hollow fiber 12 to islets 14 as the blood flows along the length of the fiber 12. In response to the provided glucose and nutrients, the islets 14 generate and secrete insulin, which diffuses from outside of hollow fiber 12 through the walls of the fiber and into the blood flowing therethrough. The insulin-containing blood (i e.. blood flowing from the device) exits fiber 12 at outlet end 18 to provide the generated insulin to the individual.

Specifically, in in vivo use of device 40, one end of hollow fiber 12 is connected by connecting means to a blood vessel, such as an artery, for receiving blood, and the opposite end of fiber 12 is connected by connecting means to a second blood vessel, such as a vein, for providing insulin-containing blood to the individual. For ex vivo use of device 40, connections other than to an artery and vein are suitable as long as blood or other medium flows through hollow fiber 12 from inlet end 16 to outlet end 18. The connecting means can be comprised of any one of various tissue compatible materials such as vascular graft material. The ends of the hollow fiber can be connected by connecting means to a single blood vessel, such as an artery or vein. Alternatively, the ends of the hollow fiber can be connected by connecting means to two blood vessels, such as an artery and a vein as described above.

Preferably, hollow fiber 12 is a porous acrylic copolymer membrane of about 100,000 Dalton average porosity, such as the type XM, manufactured by the Amicon Division of W.R. Grace & Co., Conn. The pore sizes selected provide a barrier to protect the xenograph from a host immune reaction. A pore size is selected on the basis that the fiber must retain >90% of an IgG solution. As a result of this protective barrier, the islets can be obtained from a variety of mammalian sources, such as canine, bovine, porcine, or human pancreatic tissue, without necessarily requiring immunomodulation of the islets or immune suppression of the recipient.

The ends of the hollow fiber are connected to a blood vessel or vessels in such a way that the inner diameter of the fiber substantially matches the inner diameter of the blood vessel, to provide smooth and continuous flow of blood. A fiber having an inner diameter which substantially matches the inner diameter of the vessel can be employed. For example, hollow fiber 12 has a uniform inner diameter of about 4 mm to about 7 mm. Such a diameter is compatible with the inner diameter of an individual's arteries and veins to which ends of fiber 12 are to be connected in in vivo use of the device. As a result the potential for clotting at vascular connective junctions is reduced. Alternatively, the hollow fiber can have an inner diameter which differs from that of a blood vessel. For example, the hollow fiber can be adapted with a connecting means which at one end substantially matches the diameter of the vessel and at an opposite end substantially matches the diameter of the fiber, thus providing smooth and continuous flow of blood from the blood vessel and into the device.

In addition, the connecting means can comprise a butt joint providing a smooth, essentially step free internal transition between the vessel and the fiber 12. The butt joint is made using a mandrel which can be either rigid or made of a deformable material. The mandrel is placed in the fiber and graft lumen to match the internal diameters. A smooth rigid rod can be utilized as a mandrel. The rod must have a tapered end that fits tightly into the lumens of both the fiber and graft. A deformable material that will expand when compressed can also be used as a mandrel. This can be placed in the lumens of the fiber and graft and expanded. The expanded material will tightly fit the graft and fiber creating a gradual transition between the fiber and graft. Once in place, adhesive can be cast around the mandrel between a slight gap left between the fiber and graft. Upon curing the mandrel can be removed and a smooth internal transition between the fiber and graft will remain.

The fiber has a wall thickness of 100–200 microns and a length sufficient to provide an inner surface area of the fiber of greater than about 60 cm$^2$, where the inner surface area of hollow fiber 12 equals the product of the length of the fiber, the inner diameter of the fiber and $\pi$. For example, an inner surface area of about 60 cm$^2$ or greater makes it possible to maintain the number of islets needed to produce the required amount of insulin. For example, for implantation into a human subject, the inner surface area of the hollow fiber can be about 100 cm$^2$ and the length of the fiber can be about 56 cm, which has been shown to be sufficient to support about 300,000 islets in vitro.

The islets 14 are introduced or seeded into the device in such a manner that the islets are distributed about hollow fiber 12. In order to insure proper distribution of islets about hollow fiber 12 and maintain the islets 14 in the desired locations about hollow fiber 12, an appropriate supporting material, such as a semi-solid matrix or suspension of the islets (referred to as an islet suspension) is used. The supporting material can be comprised of various substances which are capable of maintaining islet viability and physically supporting the islets in suspension. For example, in one embodiment, a semi-solid matrix is formed by adding islets to a solution of nutrient medium and liquified alginate or agar to form a suspension. The suspension is introduced in such a manner that the islets are distributed around the outside of fiber 12 and allowed to form a semi-solid which suspends the islets 14 about fiber 12. In the case of agar, the suspension is introduced and then cooled, resulting in formation of a semi-solid support. In the embodiment using alginate to form a semi-solid matrix to suspend the islets, a crosslinking agent, such as calcium chloride is also included with the alginate to crosslink the alginate into a polymer.

The housing can be comprised of plastic (e.g., polyacrylic), stainless steel, titanium or other implantable metallic substance. For example, the housing can be polycarbonate, polysulfone, polymethyl methacrylate or mixtures thereof. The housing must be tissue compatible and sufficiently inflexible to protect hollow fiber 12 and is preferably lightweight. In the embodiment illustrated in FIG. 1, extruded plastic housing 42 is generally cylindrical in shape and is as long as hollow fiber 12. Housing 42 coaxially encompasses hollow fiber 12, which lies substantially straight and curveless within housing 42. Inner walls of housing 42 form a chamber 34 about the outer surface of fiber 12. Preferably, the islet suspension is distributed circumferentially and longitudinally along the length of hollow fiber 12 in this chamber 34.

In the embodiment shown in FIG. 2, housing 20 is generally tubular in shape and follows the contour of hollow fiber 12 which is, for example, about 22 inches long. More specifically, housing 20 is coaxially positioned about fiber 12 along the length of fiber 12 and housing 20 together with fiber 12 are coiled about a longitudinal axis to provide a space saving compact device 10. In such a configuration, inner walls of housing 20 form a chamber about the outer surface of hollow fiber 12. It is into this chamber that the islet suspension is introduced and forms a semi-solid matrix about fiber 12 such that fiber 12 is surrounded along its length by islets 14.

A preferred embodiment of the present invention is illustrated in FIGS. 3a and 3b and is generally referenced 30. Hollow fiber 12 is coiled into one or more loops about a longitudinal axis, and the coiled fiber is enclosed in an annular shaped housing 22. In this configuration, each loop formed by hollow fiber 12 within housing 22 may be spaced apart from a preceeding and succeeding loop by spacers 24. The spacers 24 ensure a gap 25 between each loop of fiber 12 and ultimately enable the islet suspension to be positioned circumferentially along the length of hollow fiber 12. To that end, the islet suspension is introduced into annular housing 22 in a manner which substantially fills gaps between loops of hollow fiber 12 as well as areas around the inner and outer curves of each loop. The islet suspension forms a semi-solid which surrounds fiber 12 along its length.

In addition, housing 22 includes injection ports 26 and 28 as shown in FIG. 3b. These ports aid in the introduction of the islet suspension into the housing in such a manner that it surrounds coiled hollow fiber 12 within the housing 22. In the present invention, the suspension is drawn through one port 26 by negative pressure generated at the other port 28.

More specifically, a syringe containing the islet suspension is positioned, as for injection, at port 26. Means for drawing air from housing 22, such as a second syringe, is positioned at port 28. The drawing means is operated so as to withdraw air from housing 22 through port 28 and thus create a current directed from port 26 through housing 22 and out port 28. Consequently, the negative pressure pulls the islet suspension from the first syringe through port 26 and into housing 22, and toward port 28.

To prevent the suspension from being withdrawn from housing 22 through port 28 once drawn into the housing, screens 32 can be attached to cover internal openings 36 of port 28. For example, screens 32 comprise a tissue compatible mesh material with apertures sufficient to prevent islets from being withdrawn (i.e., smaller than the islets). For example, screens with 20–30 micron wide apertures such as of the Nytex® brand or similar type can be used. Screens 32 are fastened to the inner walls of housing 22 over openings 36 by common methods and means, including tissue compatible epoxies.

Furthermore, hollow fiber 12 exits the annular shaped housing 22 so that one end 16 of hollow fiber 12 is connected to a blood vessel, such as an artery, in such a manner that blood flows into, through and out of the device. An opposite end 18 of hollow fiber 12 is connected to a second blood vessel, such as a vein, for providing insulin-containing blood to an individual, as described in FIG. 1.

The annular shaped housing 22 may also provide one or more suture sites 38, through which the device 30 is anchored to the individual.

In an alternative embodiment to the device 30 of FIGS. 3a and 3b, the annular housing is designed to be particularly lightweight. Such a lightweight annular housing is illustrated in an exploded view in FIG. 3c and is described below.

Figure 8:
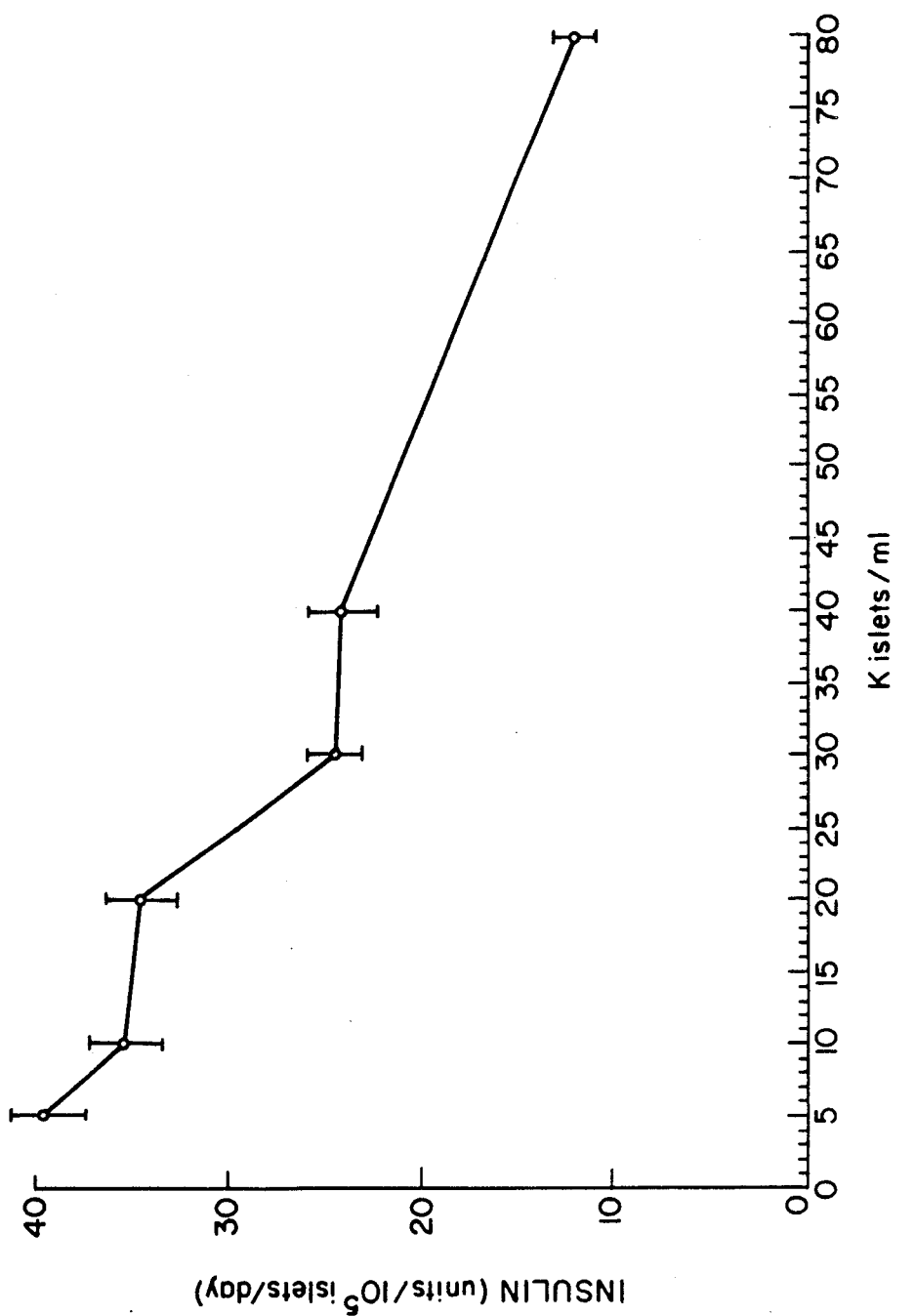

A bottom half 44 is machined from acrylic with a figure-8 central cavity 68, an inner circumferential groove 54, two bores 56 (preferably 1/16 inch diameter) leading into the circumferential groove 54 and suture sites 64 about the exterior. The hollow fiber 12 sits coiled in groove 54 with ends 16 and 18 attached to connecting means, such as vascular grafts 52 for in vivo use of the device 60. Further, the housing bottom half 44 is shaped to accommodate vascular grafts 52 connected to the fiber ends 16 and 18 to allow these grafts to protrude from the housing. In addition, a butt joint can be made using a mandrel as described previously to provide a smooth, essentially step free internal transition between the fiber and graft lumen. Optionally, a screen, such as the screen 32 described in FIG. 3b, can be attached to the wall of groove 54 to cover the opening of bore 56 in the groove to prevent drawing of islets out of the housing during introduction of the islet suspension into the housing.

A housing top half 46 is machined from acrylic with a figure-8 central cavity 68, openings 58 and an inner circumferential groove which match respectively the figure-8 central cavity 68, bores 56 and inner groove 54 in bottom half 44. Housing top half 46 is welded or otherwise hermetically sealed to bottom half 44 with respective matching parts aligned. Snapped into openings 58 are injection port assemblies 48. Each injection port assembly 48 includes a silicon plug 50 inside a cap 62, as is common in the art. The port assemblies 48 positioned in openings 58 provide the injection ports or sites for introducing the islet suspension to hollow fiber 12 coiled within the housing inner groove 54. Alternatively, injection sites could be welded into either the housing top half 46 or bottom half 44.

After the housing top half 46 and bottom half 44 have been welded together, a tissue compatible adhesive is applied to where the housing meets the connecting means to ensure a hermetic seal. Epoxy of medical grade, such as T674 manufactured by Emerson and Cumings, Inc., is preferred.

Because of the central cavity, the device 60 with the islet suspension surrounding fiber 12 weighs about 40 grams. Planar covers, of silicon or like material, for the top and bottom sides of the housing cover the figure-8 central cavity and prevent fluid from building up within the cavity during in vivo use of the device 60 without adding substantial weight. Such covers are attached to the respective outer surfaces of housing top half 46 and bottom half 44 by welding, adhesive or other methods and means common in the art.

It is understood that other configurations of the present invention are possible. Such configurations need only ensure the distribution of islets about hollow fiber 12, preferably circumferentially and longitudinally about fiber 12, such that fiber 12 is surrounded along its length by the islets 14. In optimizing the design of a configuration, it is understood that the distance between the islets and hollow fiber 12 needs to be minimized to maximize diffusion of substances, including substances which stimulate insulin secretion, as well as nutrients and oxygen, from the blood to the islets.

Preparation of islets and their introduction into the device is carried out as follows. Pancreatic islets of Langerhans are isolated from any one of various mammalian pancreatic tissues, for example canine, bovine, porcine, or human. The term "islet" or "islets" as used herein includes the constituent cell types within the islet of Langerhans, including beta cells, the actual producers of insulin, intact islets, islet fragments or combinations thereof. The procedure for isolating islets from the exocrine tissue of the donor pancreas is described in Example I.

Islets of Langerhans are suspended in an appropriate supporting material, such as liquified agar or alginate. Additional components, such as collagen and laminin and/or growth factors can be added to the islet suspension. For example, approximately 100 μg/ml of collagen I, approximately 80–100 μg/ml of collagen IV and approximately 5–10 μg/ml of laminin can be added to the islet suspension.

The islet suspension can also contain other cells which enhance islet viability. The presence of endothelial cells or fibroblasts can create an environment more like that in which islets occur naturally. Other cell types which produce growth factors or basement membrane components can be cultured with the islets to enhance growth and viability. In addition, an endothelial cell layer at the graft site can contribute to increased patency of the anastomosis site.

The liquified islet suspension is introduced to the outside of hollow fiber 12 and allowed to form a semi-solid matrix which suspends the islets in their respective locations about hollow fiber 12. If agar is used, the suspension is introduced to the outside of hollow fiber 12 and cooled to <45° C. resulting in a semi-solid support. However, if alginate is used, a crosslinking agent, such as calcium chloride, is also included with the alginate to crosslink the alginate into a polymer.

Inlet end 16 and outlet end 18 are attached to connecting means, such as vascular graft material, for example polyurethane, polytetrafluorethylene, or Dacron ™ (EI duPont de Nemours & Co.). The inlet end 16 graft material is surgically connected to a blood vessel and the outlet end 18 graft material is surgically connected to a second blood vessel, and blood flow is established through the fiber by means well known in the art.

EXAMPLE I

Isolation of Islets From Pancreatic Tissue

Islets of Langerhans were obtained from pancreata of donor animals (e.g., dog, cattle, pig). Islets of Langerhans were isolated and purified by a modification of published procedures, Moskalewski, S., *Gen. Comp. Endo.*, 5: 342 (1965); Lacy, P. E. and M. Kostianovsky, *Diabetes*, 16: 35 (1967); Lacy, P. E. et al., *Diabetes*, 31(*Suppl.* 4): 109 (1982). Briefly, the pancreas was infused via the pancreatic duct with a suspension of collagenase which digested connective tissue and disrupted the integrity of the gland. The gland was further dissociated by shaking with marbles until tissue fragments were reduced to a size of less than 500 microns diameter. This dissociation procedure released islets from the exocrine tissue that surrounded them. Islets were then separated from non-islet tissue by centrifugation on a discontinuous gradient of Ficoll ™ (Pharmacia Fine Chemicals, Inc.) (27% w/v; 23.5% w/v; and 11% w/v), which utilized the difference in density of cell types to permit islets (lower density) to be positioned at the interface of the 11% and 23.5% Ficoll layers, while non-islet tissue separated under centrifugation. Islets were collected, washed, and plated into culture plates until used.

EXAMPLE II

Agar Embedding Protocol

The 2% (wt/vol) agar gel (Sterile Bacto-Agar Difco) was liquified by heating. The volume of suspension necessary for embedding in a device was one-half of the cell compartment volume (e.g. cell chamber volume of 6 ml). An islet pellet was obtained by collecting isolated islets and centrifuging. This pellet was brought up to a volume of 3 ml (½ of cell chamber volume of 6 ml) with the addition of 2X media M199/EBSS (media 199; Earls Balanced Salt Solution). To the islet-media suspension, 3 ml of 2% agar suspension plus additives (e.g., collagen, laminin, growth factors) were added. The final concentrations of compounds used in the seeding of the islets in the device were:

| | |
|---|---|
| 1% agar | 100 μg/ml collagen I |
| 1X media | 100 μg/ml collagen IV |
| | 5 μg/ml laminin |

Figure 3C:
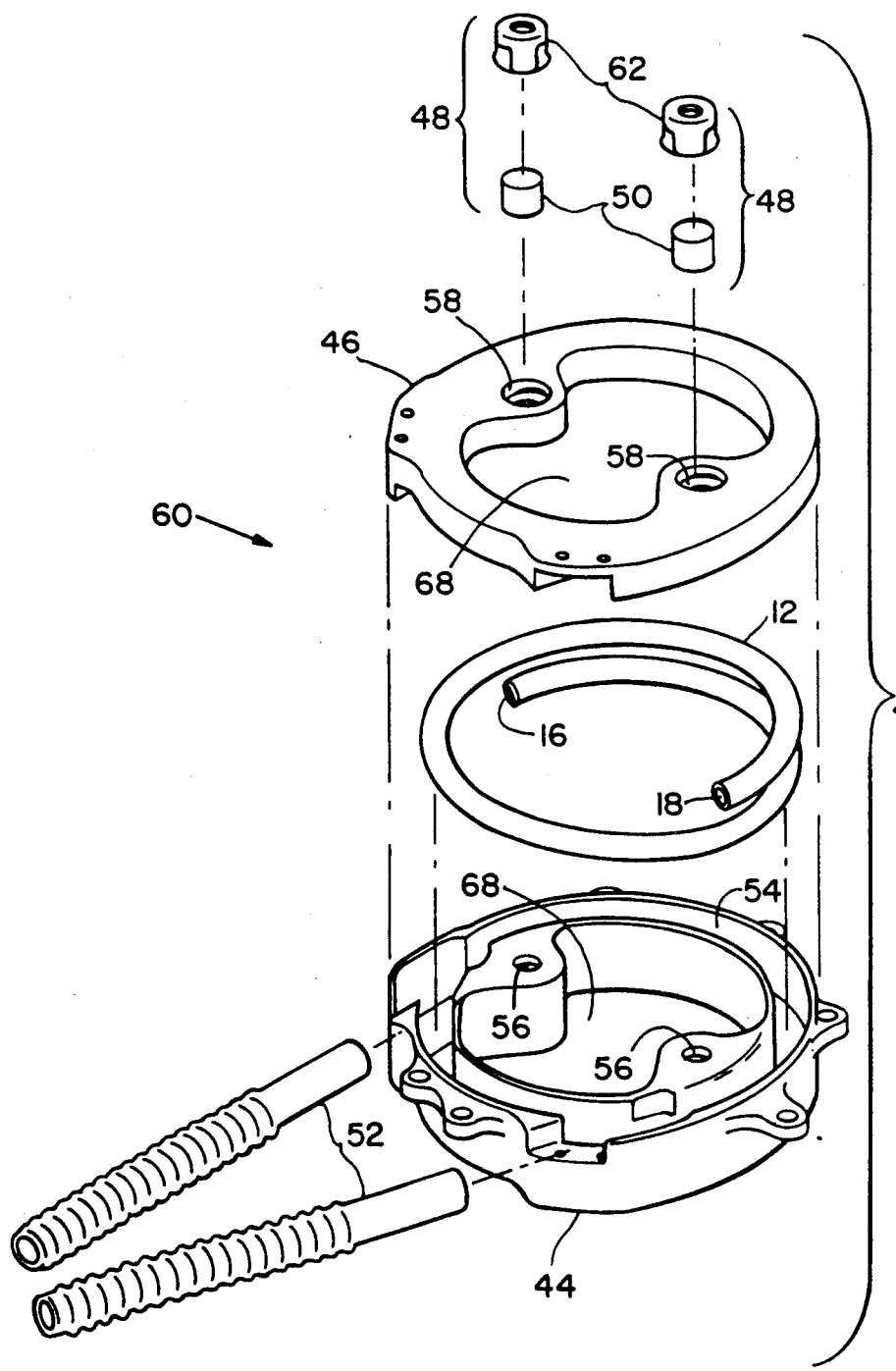
FIG. 3c is an exploded view of another embodiment having a lightweight annular housing.

The islet suspension was seeded through injection ports as in FIGS. 3b and 3c, or distributed by some other means as in FIGS. 1-3a. In the case of agar, the suspension was applied to the device and then placed on ice for approximately 10-15 minutes to effectively gel the agar prior to implantation to effectively gel the agar to form a matrix in which the islets were suspended. In the case of alginate, calcium chloride and alginate were combined to crosslink the alginate into a polymer.

EXAMPLE III

In Vitro Insulin Secretion in Artificial Pancreatic Devices

Coil Devices

Islets were seeded into devices as described in FIGS. 3a, 3b and 3c following the embedding procedure in Example II above. The coiled devices had the following characteristics:

fiber porosity: 50,000 Dalton MW-80,000 Dalton MW
fiber inner diameter: ~4.2-5.9 mm
fiber wall thickness: ~120-140 microns
surface area of fiber: 63-80 cm$^2$
cell compartment volume: ~4.5-7.5 ml In in vitro culture, seeded devices were attached to a peristaltic pump with a circulating suspension comprising M199, Earl's Balanced Salt Solution and 5% fetal bovine serum. The medium was changed every 2 days and a sample was taken to measure insulin units by radioimmunoassay.

Figure 4:
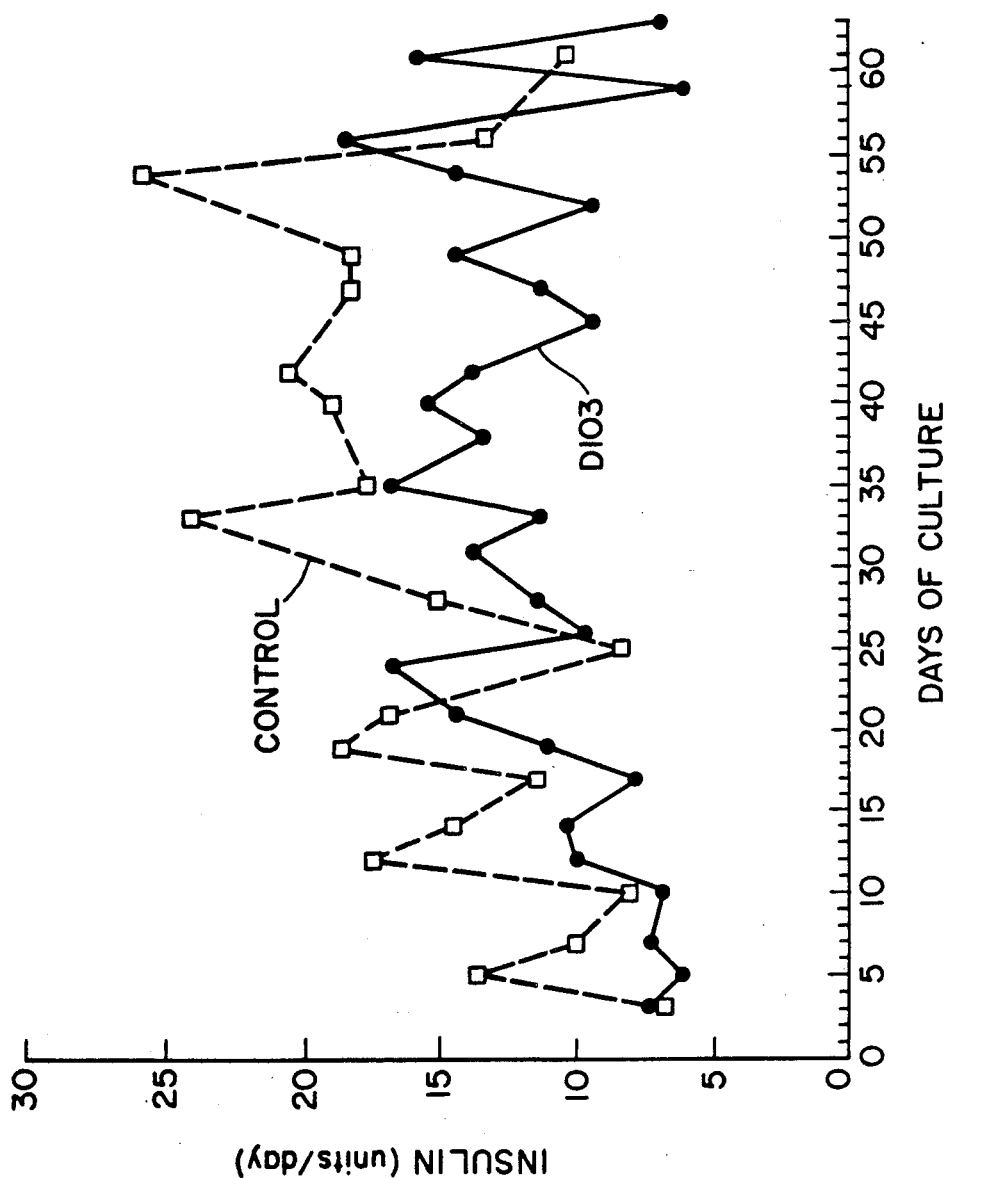
FIGS. 4–6 are graphic representations of in vitro insulin output in three separate coil devices embodying the present invention.
Figure 5:
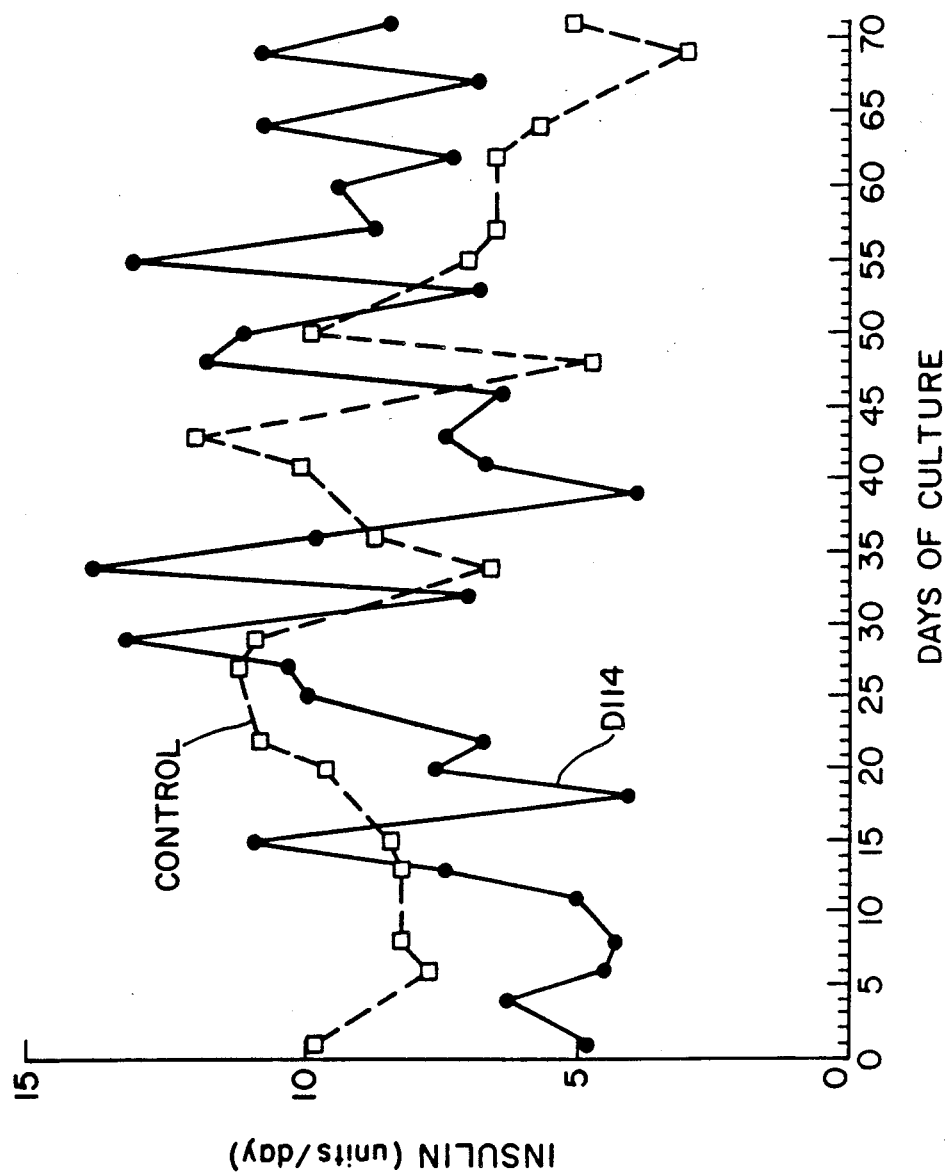
Figure 6:
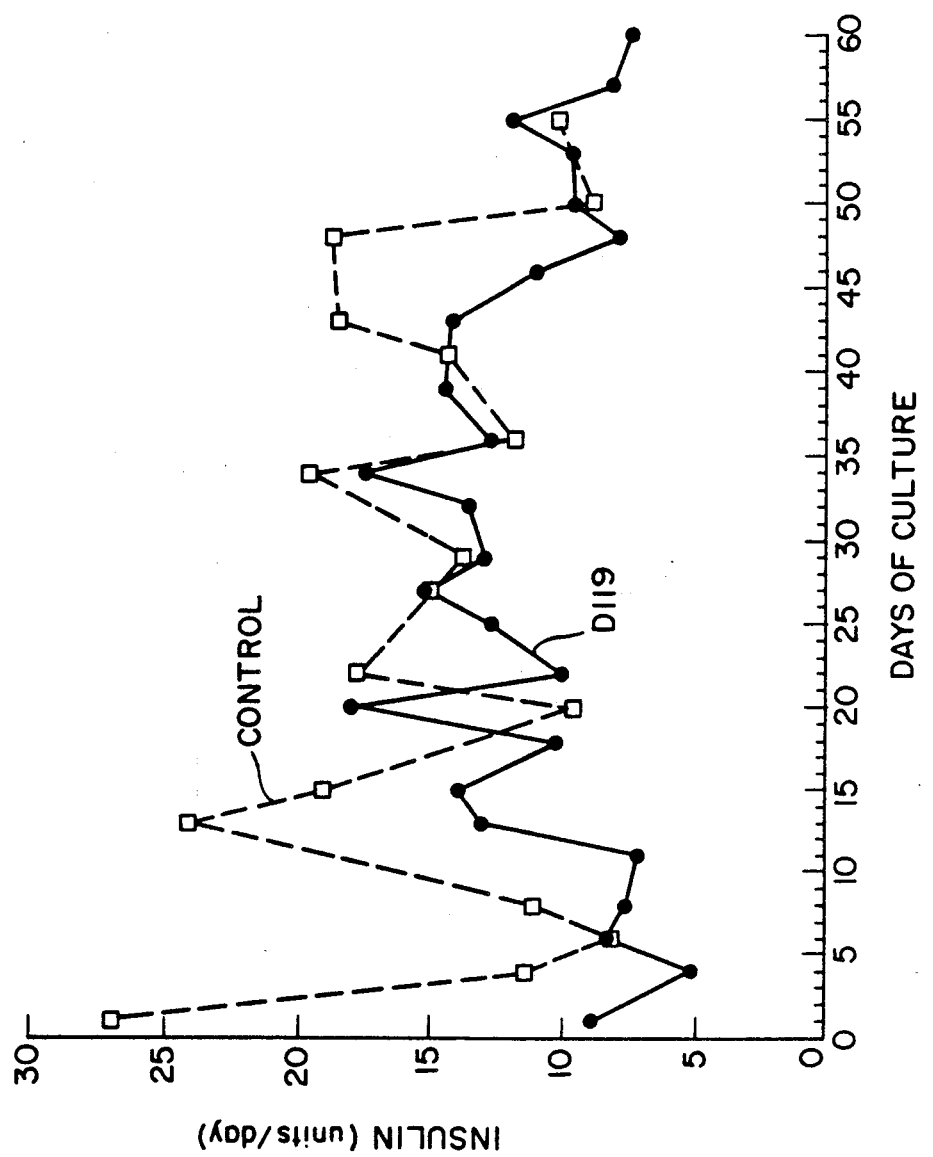

Insulin secretion by the embedded islets averaged 52 ±6% of the control values obtained from islets free in culture (n=6) over a period of time ranging from one week to four months. The control output is based on insulin secretion from a sampling of the same islet preparation maintained in culture. The addition of soluble matrix factors, collagen I, collagen IV and laminin, further enhanced insulin secretion. In the presence of these additives, insulin secretion averaged 74±5% of predicted (n=30) from devices in culture for 2 weeks to 3 months. Data from 3 of these devices are shown in FIGS. 4-6 and demonstrate that the isolated islets remain viable and continue to secrete insulin for several months in vitro.

Straight Devices

Figure 7:
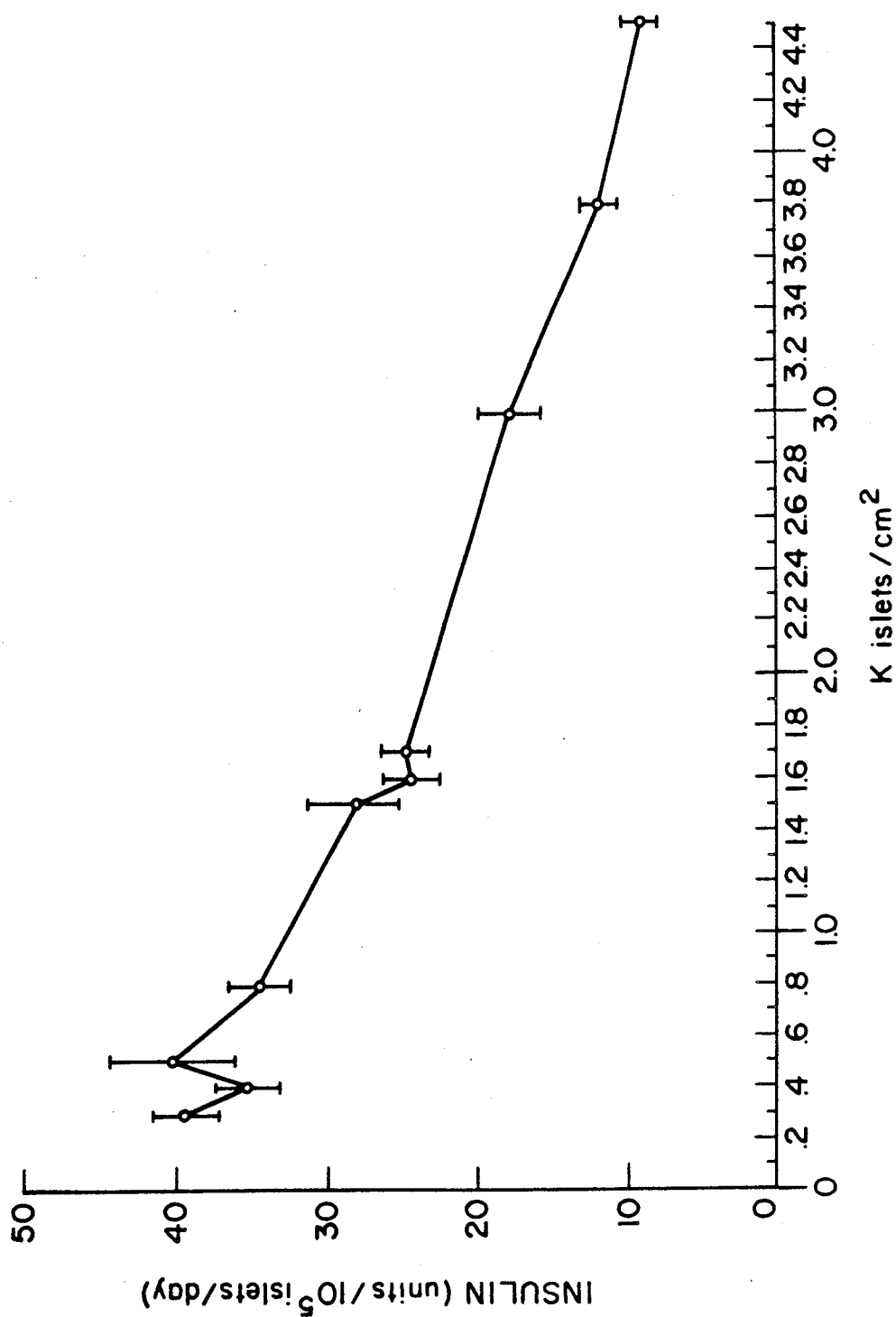
FIGS. 7 and 8 are graphic representations of the correlation between islet seeding density, surface area and insulin output.

Insulin secretion has also been evaluated using agar embedded islets seeded into straight devices, described in FIG. 1. These devices were attached to a peristaltic pump and the same procedures as described above for the coil device were followed. The straight devices have been particularly useful for studies of the effect of seeding density (number of islets per ml of chamber volume) and fiber surface area (number of islets per cm$^2$ fiber).

fiber length: 12.7 cm, 19 cm and 38 cm
fiber diameter: 5.8 mm, 6.2 mm and 6.6 mm
surface area: 30, 49, 56, and 64 cm$^2$
cell compartment volume: 1.3-2.8 ml
void volumes: 0.8 ml-6.2 ml Insulin output from islets in the straight devices has been excellent, averaging 200%+/−22% of control values (n=19). The correlation between insulin output and seeding density for fiber surface area is shown in FIGS. 7 and 8. As with the coils, these data also demonstrate long term viability and secretory responsiveness since six straight devices have now been in culture for 6 to 9 months.

EXAMPLE IV

In vivo Long Term Patency Studies of Artificial Pancreatic Devices

A total of 37 in vivo unseeded, perfusion devices have been implanted in normal dogs. Of those, 9 animals which had complications during or immediately following surgery are not included in the following averages:

During the first phase of surgeries, 10 devices achieved an average patency of 9 days and a maximum level of 18 days, as surgical technique and device design underwent extensive development. With practice, surgeons improved the anastomoses, and techniques for heparinization and reduced infections were optimized. In the device, membrane graft junctions were improved to create a smoother path of blood flow. The surgical implantation site initially chosen for these devices was the femoral area of the dog, with the device acting as an arteriovenous shunt. Two to three days prior to device implantation, a natural shunt was placed in the dog and the device was subsequently anastomosed to this shunt. Complications may have resulted because the animals were subjected to repeated surgeries.

Patency rates improved during phase two; of 8 devices, the average remained patent for 84 days while the longest ran for 144. Device design improvements, in addition to a new implantation site, helped to increase device life. Devices were anastomosed to the carotid artery and jugular vein in the neck, and cleaner, more sterile techniques, were adopted. Five of these devices failed because they became dislocated, resulting in an external graft bend of 90° and blood flow interruption. In addition, blood flow through several devices was interrupted due to tissue ingrowth at the graft anastomosis site, a common cause of failure with commercial arteriovenous shunts.

The last series of 10 long-term patency devices were anastomosed to either the carotid artery and jugular vein or to the common iliac artery and vein in the groin. Of the 3 devices implanted in the groin, the average patency was 38 days while the maximum life was 76 days. Failures often resulted because of device migration or clotting at the anastomosis site. Of the 7 devices implanted in the neck, the average patency was 50 days while the maximum life was 189. During this phase, most junctions between the hollow fiber and the graft material were epoxied differently than in phase two, causing a less smooth path of blood flow and consequent clotting. A new technique similar to the older, more successful method was adopted and the device life increased to over 6 months.

EXAMPLE V

In vivo Insulin Secretion in Seeded Artificial Pancreatic Devices

Diabetes was pharmacologically induced in a dog by administering a combination of alloxan and streptozotocin. A coil device (FIGS. 3a, 3b and 3c) containing embedded canine islets was implanted into the diabetic animal. Prior to implantation, the dog had been maintained on approximately 6 units of insulin per day. After induction, the K rate (measure of glucose clearance from the circulation after an intravenous glucose injection) decreased from a value of 4.1 to 0.9. Four glucose tolerance tests (GTT) were performed while the device was implanted in the dog. Although no supplemental insulin was administered during this period, the K rate increased to 2.5±0.4 (X±SEM).

After 30 days, the device was removed from the animal for histological evaluation of the seeded islets. The results indicated the presence of healthy islets (80% viability) in the agar matrix.

A second device was implanted into a diabetic animal for eight weeks. The insulin output from the device (approximately 4 units per day) was not sufficient to restore normoglycemia during the period of the implant. However, histological evaluation again indicated that the islets had remained healthy (75% viability) in the device for eight weeks in vivo. These preliminary data demonstrate that the device described will support islet viability in vivo and, in one case, has resulted in improved glucose regulation in a diabetic dog.

Equivalents

While this invention has been particularly shown and described with references to preferred embodiments thereof, it will be understood by those skilled in the art that various changes in form and details may be made therein without departing from the spirit and scope of the invention as defined by the appended claims.

We claim:

1. An artificial pancreatic perfusion device for providing insulin to an individual, the device comprising:
   (a) a hollow fiber having one end connected to a blood vessel through a connecting means to receive blood from the individual and an opposite end connected to a blood vessel through a second connecting means to return blood to the individual, the hollow fiber having a porosity which selectively allows substances to pass transversely therethrough, such that blood flows within the hollow fiber, along the length of the fiber; and
   (b) a housing containing a suspension of pancreatic islets of Langerhans, the suspension including pancreatic islets distributed in an appropriate supporting material about the hollow fiber such that the hollow fiber is surrounded by pancreatic islets along its length, the supporting material maintaining distribution and desired location of the islets with respect to the hollow fiber.

2. An artificial pancreatic perfusion device as in claim 1, wherein the hollow fiber has a porosity which allows for passage only of substances of molecular weight of less than 100,000 Daltons.

3. An artificial pancreatic perfusion device as in claim 1 wherein the supporting material is distributed circumferentially and longitudinally about the hollow fiber.

4. An artificial pancreatic perfusion device as in claim 1, wherein the supporting material comprises a semi-solid matrix for suspending islets, the semi-solid matrix being positioned about the hollow fiber to surround the fiber.

5. An artificial pancreatic perfusion device as in claim 1 wherein the supporting material is introduced to the hollow fiber in a liquid form and maintained under appropriate conditions to form a semi-solid matrix.

6. An artificial pancreatic perfusion device as in claim 5 wherein said supporting material comprises agar or alginate.

7. An artificial pancreatic perfusion device as in claim 1 wherein the housing encloses the hollow fiber in a spaced apart manner, such that the housing defines a chamber circumferentially about the hollow fiber along the length of the fiber, the housing being positioned sufficiently close to the fiber along the length of the fiber to maximize diffusion across the fiber wall.

8. An artificial pancreatic perfusion device as in claim 7 wherein the housing is cylindrical in shape and the hollow fiber is coaxially positioned therein.

9. An artificial pancreatic perfusion device as in claim 7 wherein:
   (a) the housing is annular in shape about a central axis; and (b) the hollow fiber is coiled about the central axis and lies within the housing in a manner spaced apart from inner walls of the housing, each loop of the coiled fiber being spaced apart from succeeding and preceding loops.

10. An artificial pancreatic perfusion device as in claim 9 further comprising spacers between successive loops of the coiled fiber to maintain the loops in a spaced apart manner.

11. An artificial pancreatic perfusion device as in claim 7 wherein the housing is a coiled tube and the hollow fiber is coaxially positioned therein.

12. An artificial pancreatic perfusion device as in claim 1 wherein the connecting means comprises vascular graft material.

13. An artificial pancreatic perfusion device as in claim 1 wherein the connecting means comprises a butt joint.

14. An artificial pancreatic perfusion device for providing insulin to an individual, the device comprising:
  (a) a hollow fiber having one end connected to a blood vessel through a connecting means to receive blood from the individual and an opposite end connected to a blood vessel through a second connecting mean to return blood to the individual, the blood flowing within the fiber along the length of the fiber, the fiber having a porosity which selectively allows substances to pass transversely therethrough; and
  (b) a housing containing a suspension of pancreatic islets of Langerhans, the suspension including pancreatic islets distributed in an appropriate supporting material about the hollow fiber in a manner which maximizes diffusion of substances from the blood within the fiber, transversely across the hollow fiber wall to the islets to stimulate generation of insulin by the islets, and maximizes passage of generated insulin transversely through the fiber wall and into the blood flowing within the fiber, the supporting material maintaining distribution and desired location of the pancreatic islets with respect to the hollow fiber.

15. An artificial pancreatic perfusion device as in claim 14 wherein the housing positions pancreatic islets circumferentially and longitudinally about the hollow fiber such that the fiber is surrounded by pancreatic islets along its length.

16. An artificial pancreatic perfusion device as in claim 14 wherein the supporting material comprises a semi-solid matrix for suspending islets, the semi-solid matrix being distributed circumferentially about the hollow fiber along the length of the fiber.

17. An artificial pancreatic perfusion device as in claim 14 wherein the housing encloses the hollow fiber in a spaced apart manner such that the housing defines a chamber circumferentially about the fiber along the length of the fiber, the housing being sufficiently close to the fiber along the length of the fiber to maximize diffusion.

18. An artificial pancreatic perfusion device as in claim 17 wherein the housing is cylindrical in shape and the hollow fiber is coaxially positioned therein.

19. An artificial pancreatic perfusion device as in claim 17 wherein:
  (a) the housing is annular in shape about a central axis; and
  (b) the hollow fiber is coiled about the central axis and lies within the housing in a manner spaced apart from inner walls of the housing, each loop of the coiled fiber being spaced apart from succeeding and preceding loops.

20. An artificial pancreatic perfusion device as in claim 19 further comprising spacers between successive loops of the coiled fiber to maintain the loops spaced apart.

21. An artificial pancreatic perfusion device as in claim 17 wherein the housing is a coiled tube and the hollow fiber is coaxially position therein.

22. A method of seeding an artificial organ with islets of Langerhans comprising:
  (a) suspending the islets in a solution consisting essentially of nutrient medium and liquified agar to thereby form an islet suspension;
  (b) injecting said suspension into said artificial organ; and
  (c) solidifying the islet suspension to thereby form a semi-solid matrix maintaining distribution and desired location of the islet cells within the housing.

23. A method of claim 22 wherein the suspension is injected by creation of negative pressure to pull islet suspension into the artificial organ.

24. A method of claim 22 wherein additional components are added to the nutrient medium to enhance islet viability, said components selected from the group consisting of: collagen, laminin and growth factors.

25. A method of claim 22 wherein the islet suspension is co-cultured with cells which enhance graft biocompatibility and islet viability, said cells selected from the group consisting of: endothelial cells, fibroblasts and cells which produce growth factors or basement membrane.

26. An artificial pancreatic perfusion device for providing insulin to an individual, the device comprising:
  (a) an annular shaped, plastic housing;
  (b) a hollow fiber coiled within the housing and spaced apart from inner walls of the housing, the hollow fiber having opposite ends adapted to be coupled to a blood vessel such that the hollow fiber through one end receives blood from the individual, the blood flows within the fiber, along the length of the fiber, and through the opposite end of the fiber supplies flowing blood to the individual, the hollow fiber having a porosity which selectively allows passage of substances transversely through the fiber wall, and having a total inner surface area adequate to support the number of islets required for insulin secretion; and
  (c) a pancreatic islet suspension including pancreatic islets distributed in an appropriate supporting material about the hollow fiber, the islet suspension surrounding the hollow fiber within the housing, and the supporting material maintaining distribution and desired location of the islets with respect to the hollow fiber, and islets within the suspension generating insulin which diffuses across the hollow fiber wall to the blood flowing within the hollow fiber in response to substances diffused across the hollow fiber wall from the blood.

27. An artificial pancreatic perfusion device for providing insulin to an individual, the device comprising:
  (a) a hollow fiber having one end connected to a blood vessel through a connecting means to receive blood from the individual and an opposite end connected to a blood vessel through a second connecting means to return blood to the individual, the hollow fiber having an inner diameter substantially matching an inner diameter of the blood vessel connected thereto and having a porosity which selectively allows substances to pass transversely therethrough, such that blood flows within the hollow fiber, along the length of the fiber; and (b) a housing containing pancreatic islets of Langerhans distributed in an appropriate supporting material about the hollow fiber such that the hollow fiber is surrounded by pancreatic islets along its length, wherein the housing is annular in shape about a central axis and encloses the hollow fiber in a spaced apart manner, such that the housing defines a chamber circumferentially about the hollow fiber along the length of the fiber, the housing is positioned sufficiently close to the fiber along the length of the fiber to maximize diffusion across the fiber wall, and the hollow fiber is coiled about the central axis and lies within the housing in a manner spaced apart from the inner walls of the housing, each loop of the coiled fiber being spaced apart from succeeding and preceding loops.

28. An artificial pancreatic perfusion device as in claim 27 further comprising spacers between successive loops of the coiled fiber to maintain the loops in a spaced apart manner.

29. An artificial pancreatic perfusion device for providing insulin to an individual, the device comprising:
(a) a hollow fiber having one end connected to a blood vessel through a connecting means to receive blood from the individual and an opposite end connected to a blood vessel through a second connecting means to return blood to the individual, the hollow fiber having an inner diameter substantially matching an inner diameter of the blood vessel connected thereto and having a porosity which selectively allows substances to pass transversely therethrough, such that blood flows within the hollow fiber, along the length of the fiber; and
(b) a housing containing pancreatic islets of Langerhans distributed in an appropriate supporting material about the hollow fiber, such that the hollow fiber is surrounded by pancreatic islets along its length,
wherein the housing is a coiled tube and the hollow fiber is coaxially positioned therein and the housing encloses the hollow fiber in a spaced apart manner, such that the housing defines a chamber circumferentially about the hollow fiber along the length of the fiber, the housing is positioned sufficiently close to the fiber along the length of the fiber to maximize diffusion across the fiber wall, and the hollow fiber is coiled about the central axis and lies within the housing in a manner spaced apart from the inner walls of the housing, each loop of the coiled fiber being spaced apart from succeeding and preceding loops.

30. An artificial pancreatic perfusion device for providing insulin to an individual, the device comprising:
(a) a hollow fiber having one end connected to a blood vessel through a connecting means to receive blood from the individual and an opposite end connected to a blood vessel through a second connecting means to return blood to the individual, the blood flowing within the fiber along the length of the fiber, the fiber having a porosity which selectively allows substances to pass transversely therethrough; and
(b) a housing containing pancreatic islets of Langerhans distributed in an appropriate supporting material about the hollow fiber in a manner which maximizes diffusion of substances from the blood within the fiber, transversely across the hollow fiber wall to the islets to stimulate generation of insulin by the islets, and maximizes passage of generated insulin transversely through the fiber wall and into the blood flowing within the fiber,
wherein the housing is annular in shape about a central axis and encloses the hollow fiber in a spaced apart manner such that the housing defines a chamber circumferentially about the fiber along the length of the fiber, the housing is sufficiently close to the fiber along the length of the fiber to maximize diffusion, and the hollow fiber is coiled about the central axis and lies within the housing in a manner spaced apart from inner walls of the housing, each loop of the coiled fiber being spaced apart from succeeding and preceding loops.

31. An artificial pancreatic perfusion device as in claim 30 further comprising spacers between successive loops of the coiled fiber to maintain the loops in a spaced apart manner.

32. An artificial pancreatic perfusion device for providing insulin to an individual, the device comprising:
(a) a hollow fiber having one end connected to a blood vessel through a connecting means to receive blood from the individual and an opposite end connected to a blood vessel through a second connecting means to return blood to the individual, the blood flowing within the fiber along the length of the fiber, the fiber having a porosity which selectively allows substances to pass transversely therethrough; and
(b) a housing containing pancreatic islets of Langerhans distributed in an appropriate supporting material about the hollow fiber in a manner which maximizes diffusion of substances from the blood within the fiber, transversely across the hollow fiber wall to the islets to stimulate generation of insulin by the islets, and maximizes passage of generated insulin transversely through the fiber wall and into the blood flowing within the fiber,
wherein the housing is a coiled tube and the hollow fiber is coaxially positioned therein, and the housing encloses the hollow fiber in a spaced apart manner such that the housing defines a chamber circumferentially about the fiber along the length of the fiber, the housing being sufficiently close to the fiber along the length of the fiber to maximize diffusion.

33. An artificial pancreatic perfusion device for providing insulin to an individual, the device comprising:
(a) a housing;
(b) a hollow fiber coiled within the housing and spaced apart from inner walls of the housing, the hollow fiber having opposite ends adapted to be coupled to a blood vessel such that the hollow fiber through one end receives blood from the individual, the blood flows within the fiber, along the length of the fiber, and through the opposite end of the fiber supplies flowing blood to the individual, the hollow fiber having a porosity which selectively allows passage of substances transversely through the fiber wall, and having a total inner surface area adequate to support the number of islets required for insulin secretion; and (c) a pancreatic islet suspension including pancreatic islets distributed in an appropriate supporting material about the hollow fiber, the supporting material maintaining distribution and desired location of the islets with respect to the hollow fiber, the islet suspension surrounding the hollow fiber within the housing, islets within the suspension generating insulin which diffuses across the hollow fiber wall to the blood flowing within the hollow fiber in response to substances diffused across the hollow fiber wall from the blood.

* * * * *